United States Patent
Arberet et al.

(10) Patent No.: US 12,315,047 B2
(45) Date of Patent: May 27, 2025

(54) DATA-CONSISTENCY FOR IMAGE RECONSTRUCTION

(71) Applicant: Siemens Healthineers AG, Forchheim (DE)

(72) Inventors: Simon Arberet, Princeton, NJ (US); Mariappan S. Nadar, Plainsboro, NJ (US); Boris Mailhe, Plainsboro, NJ (US); Mahmoud Mostapha, Princeton, NJ (US); Nirmal Janardhanan, Monmouth Junction, NJ (US)

(73) Assignee: Siemens Healthineers AG, Forchheim (DE)

( * ) Notice: Subject to any disclaimer, the term of this patent is extended or adjusted under 35 U.S.C. 154(b) by 677 days.

(21) Appl. No.: 17/457,948

(22) Filed: Dec. 7, 2021

(65) Prior Publication Data
US 2022/0215600 A1    Jul. 7, 2022

(30) Foreign Application Priority Data
Jan. 5, 2021   (EP) .................................... 21150346

(51) Int. Cl.
| | |
|---|---|
| G06K 9/00 | (2022.01) |
| G01R 33/56 | (2006.01) |
| G06N 3/04 | (2023.01) |
| G06T 11/00 | (2006.01) |
| G16H 30/40 | (2018.01) |

(52) U.S. Cl.
CPC ........ *G06T 11/008* (2013.01); *G01R 33/5608* (2013.01); *G06N 3/04* (2013.01); *G16H 30/40* (2018.01)

(58) Field of Classification Search
None
See application file for complete search history.

(56) References Cited

U.S. PATENT DOCUMENTS

| | | | |
|---|---|---|---|
| 2020/0065969 A1 | 2/2020 | Huang et al. | |
| 2020/0294287 A1* | 9/2020 | Schlemper | ................ G06T 5/70 |

OTHER PUBLICATIONS

Malkiel et al., "Densely connected iterative network for sparse MRI reconstruction" (Year: 2018).*
Akcakaya, M., et al. "Iterative compressed sensing reconstruction for 3d non-cartesian trajectories without gridding & regridding at every iteration." Proceedings of the annual meeting of ISMRM. vol. 19. 2011. p. 2550.
Antun, Vegard, et al. "On instabilities of deep learning in image reconstruction—Does AI come at a cost?." arXiv preprint arXiv:1902. 05300 (2019).

(Continued)

*Primary Examiner* — S J Park (57) ABSTRACT

A computer-implemented method includes, based on an input dataset defining an input image, determining a reconstructed image using a reconstruction algorithm, and executing a data-consistency operation for enforcing consistency between the input image and the reconstructed image. The data-consistency operation determines, for multiple K-space positions at which the input dataset comprises respective source data, a contribution of respective K-space values associated with the input dataset to a K-space representation of the reconstructed image.

19 Claims, 4 Drawing Sheets

(56) References Cited

OTHER PUBLICATIONS

Goodfellow, Ian; Pouget-Abadie, Jean; Mirza, Mehdi; Xu, Bing; Warde-Farley, David; Ozair, Sherjil; Courville, Aaron; Bengio, Yoshua (2014), Generative Adversarial Networks. Proceedings of the International Conference on Neural Information Processing Systems (NIPS 2014). pp. 2672-2680.

Hammernik, Kerstin, et al. "Learning a variational network for reconstruction of accelerated MRI data." Magnetic resonance in medicine 79.6 (2018): 3055-3071.

Knoll, Florian, et al. "Deep learning methods for parallel magnetic resonance image reconstruction." arXiv preprint arXiv:1904.01112 (2019). pp. 1-14.

Malkiel, Itzik, et al. "Densely Connected Iterative Network for Sparse MRI Reconstruction." ISMRM 26th Annual Meeting. 2018. p. 3363.

Ronneberger, Olaf, Philipp Fischer, and Thomas Brox. "U-net: Convolutional networks for biomedical image segmentation." International Conference on Medical image computing and computer-assisted intervention. Springer, Cham, 2015. pp. 1-8.

Yip, Eugene, et al. "Prior Data Assisted Compressed Sensing—A Novel Strategy for Real Time Dynamic MRI." Proc. Intl. Soc. Mag. Reson. Med. vol. 22. 2014. p. 4372.

Zhu, Bo, et al. "Image reconstruction by domain-transform manifold learning." Nature 555.7697 (2018): 1-18.

Malkiel Itzik et al:; "Conditional WGANs with adaptive gradient balancing for sparse MRI reconstruction"; May 2, 2019; arXiv preprint arXiv:1905.00985.

\* cited by examiner

DATA-CONSISTENCY FOR IMAGE RECONSTRUCTION

RELATED APPLICATION

This application claims the benefit of EP 21150346, filed Jan. 5, 2021, which is hereby incorporated by reference in its entirety.

TECHNICAL FIELD

Various examples generally relate to image reconstruction. Various examples specifically relate to enforcing data consistency in connection with the image reconstruction.

BACKGROUND

Image reconstruction is used for various use cases. Examples include increasing an image resolution and reducing artifacts or noise included in an image. For example, image reconstruction can be used for medical image datasets. Image reconstruction can also be used for post-processing microscopy images or movie clips.

Various reconstruction algorithms are known. One example type of reconstruction algorithm employs machine learning. Such machine-learned reconstruction algorithms often show improved image quality compared to traditional reconstruction techniques, however, one of the limitations is the risk of hallucinating structures, or other stability issues such as e.g., an unpredicted behavior when an input is too different from what the network has been trained on, which is of special concern for medical image application.

For example, image reconstruction using generative adversarial networks (GANs) has been described in: Goodfellow, Ian; Pouget-Abadie, Jean; Mirza, Mehdi; Xu, Bing; Warde-Farley, David; Ozair, Sherjil; Courville, Aaron; Bengio, Yoshua (2014). Generative Adversarial Networks. Proceedings of the International Conference on Neural Information Processing Systems (NIPS 2014). pp. 2672-2680.

Other examples include black-box networks such as AUTOMAP, see B. Zhu, J. Z. Liu, S. F. Cauley, B. R. Rosen and M. S. Rosen, 'Image reconstruction by domain-transform manifold learning', Nature, vol. 555, no. 7697, p. 487, March 2018. Unrolled networks have been used to reconstruct magnetic-resonance imaging datasets, see Antun, V., Renna, F., Poon, C., Adcock, B., & Hansen, A. C. (2019). On instabilities of deep learning in image reconstruction-Does AI come at a cost?. arXiv preprint arXiv:1902.05300.

Generally, for various types of image reconstruction algorithms, it is desirable to enforce consistency between the input image and the reconstructed image. In other words, artifacts stemming from the reconstruction algorithm itself should be avoided or reduced. Unforeseen deviations between the input image and the reconstructed image should be avoided. This is generally achieved by a data-consistency operation (DCO).

SUMMARY

Accordingly, there is a need for advanced techniques of determining a reconstructed image based on an input dataset defining an input image. In particular, there is a need for advanced techniques that help to enforce consistency between an input image defined by an input dataset and the reconstructed image.

Various examples of the disclosure generally relate to image reconstruction. According to various examples, a reconstruction algorithm is used to determine a reconstructed image. A DCO—that may be embedded into the reconstruction algorithm or may be separately defined—is applied to the reconstructed image, to thereby enforce a consistency between an input image that is defined by an input dataset, as well as the reconstructed image.

The DCO may also be termed data-fidelity operation or forward-sampling operation.

The DCOs described herein facilitate accurate reconstruction with little or no artifacts stemming from the reconstruction algorithm itself. The DCOs described herein are computationally inexpensive.

According to various examples, a specific type of DCO is used. According to various examples, the DCO determines, for multiple K-space positions at which the input dataset includes respective source data, a contribution of respective K-space values associated with the input dataset to a K-space representation of the reconstructed image.

In other words, the DCO can, at least to a certain degree, override or undo contributions of the reconstruction algorithm, so that at K-space positions where source data is available, the respective values of the K-space representation of the reconstructed image obtained from the reconstruction algorithm are replaced fully or partly by respective values of the source data.

Thus, the reconstructed image obtained from the reconstruction algorithm prior to the DCO can be labelled preliminary reconstructed image or pre-DCO reconstructed image; and the reconstructed image obtained after applying the DCO is the final reconstructed image or post-DCO reconstructed image. I.e., where source data is available in the input dataset, this source data can prevail in the final reconstructed image or, at least, significantly contribute to the K-space values of the K-space representation of the final reconstructed image. On the other hand, where the source data is not available in the input dataset, no contribution of respective K-space values associated with the input dataset may be made to the K-space representation of the final reconstructed image.

Various examples of the disclosure also relate to a method of training of a machine-learned reconstruction algorithm. According to various examples, a machine-learned reconstruction algorithm is trained using a loss function. The loss function is based on a difference between a ground truth image and the reference image. The reference image is determined based on a training dataset that is associated with the ground truth image and using the machine-learned reconstruction image. The reference image is further determined based on executing a data-consistency operation. The data-consistency operation determines, for multiple K-space positions at which the training dataset includes respective source data, a contribution of respective K-space-values associated with the training dataset to a K-space representation of the reference image.

By considering the data-consistency operation in the training process, i.e., by using a loss function that is based on the difference between the ground truth image and the reference image that has been determined based on executing the data-consistency operation, the machine-learned reconstruction image can be accurately trained, in particular, taking into consideration alterations to its output made by the data-consistency operation. For example, spatial frequencies in the reference image that are modified by the contribution determined by the data-consistency operation may not be overemphasized in the training process. The training can focus on other spatial frequencies not modified by the contribution determined by the data-consistency operation.

It is to be understood that the features mentioned above and those yet to be explained below may be used not only in the respective combinations indicated, but also in other combinations or in isolation without departing from the scope of the invention.

DETAILED DESCRIPTION OF EMBODIMENTS

Some examples of the present disclosure generally provide for a plurality of circuits or other electrical devices. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments of the invention will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

Various examples of the disclosure generally relate to image reconstruction. An input dataset is obtained. As a general rule, the techniques described herein can be applicable to various image reconstruction tasks. For instance, image reconstruction of medical images, e.g., MRI image or computer tomography (CT) images would be possible. Microscopy images could be reconstructed, e.g., to achieve super resolution and/or remove artifacts. Photography is could be reconstructed, e.g., to remove flares. X-ray images could be reconstructed, e.g., to make certain structures otherwise hidden visible.

The input dataset can be obtained from a data storage. The input dataset can be obtained from a measurement device, e.g., a multi-pixel detector, radio-frequency receivers, etc.

The input dataset can include source data. The source data could be implemented by K-space data samples or by image-domain pixels or voxels.

The input dataset defines an input image. According to some examples, the input dataset may include the input image. I.e., the input dataset may be defined in spatial domain. For instance, an optical microscope may be used to obtain the input image. According to further examples, the input dataset may be defined in K-space. Examples would include acquisition of a magnetic resonance imaging (MRI) measurement dataset. Here, a Fourier transformation is required to obtain the input image from the input dataset.

Example input datasets include source data such as raw measurement in an MRI K-space-to-image reconstruction, or, e.g., a low-resolution image in the case of a super-resolution image-to-image reconstruction.

As a general rule, the particular type of the reconstruction algorithm is not germane for the functioning of the techniques described herein; in other words, the techniques described herein can be flexibly combined with various kinds and types of reconstruction algorithms. For instance, depending on the particular source of the input dataset, different types of reconstruction algorithms may be appropriate to use. For instance, to suppress artifacts in a microscopy image, a respective image reconstruction algorithm may be used, e.g., correcting aberrations introduced by the objective lens, creating super-resolution, etc. Differently, to remove undersampling aliasing artefacts from an MRI measurement data acquired with an undersampling K-space trajectory, a respective image reconstruction algorithm tailored to this task may be used.

According to various examples, a machine-learned reconstruction algorithm may be used. Examples would include variational or unrolled networks for reconstruction of undersampled MRI measurement data, see, e.g., Hammernik, Kerstin, et al. "Learning a variational network for reconstruction of accelerated MRI data." *Magnetic resonance in medicine* 79.6 (2018): 3055-3071. Another example would be GANs or AUTOMAP algorithms, as described above.

Irrespective of the particular implementation of the image reconstruction algorithm, according to various examples, a DCO is used, to thereby enforce a consistency between the reconstructed image and the input image defined by the input dataset.

For instance, the preliminary reconstructed image obtained from the image reconstruction algorithm may be altered or amended, at least at certain positions in image domain or in K-space (i.e., for certain spatial frequencies), when applying the DCO. Such altering or amending of the data underlying the preliminary reconstructed image can be done to increase a similarity value between the input image and the final reconstructed image.

Thus, by the DCO, generally the quality of the image reconstruction can be increased.

The DCOs described herein can operate in K-space. I.e., different K-space positions may be treated differently by the DCO. Different spatial frequencies may be affected differently by the DCO.

According to various examples, the DCO determines, for multiple K-space positions at which the input dataset includes respective source data (e.g., measurement data or generally data that is initially available before applying any reconstruction), a contribution of respective K-space values associated with the input dataset to a K-space representation of the reconstructed image.

Thus, the DCO can select, for each one of the multiple K-space positions where source data is natively available, to include the respective source data in the reconstructed image, at least to a certain degree.

As a general rule, the DCO may be defined separately from the reconstruction algorithm or may be integrated into the reconstruction algorithm.

For example, in case of an iterative optimization including multiple iterations, the DCO can be applied in each iteration.

For example, in case of an unrolled neural network, each layer of the unrolled neural network may be followed by applying the DCO.

For a K-space-to-image reconstruction, the input dataset is natively defined in the K-space and the available source data includes the acquired K-space values. In the case of an image-to-image reconstruction, the source data or more specifically the input image included in the input dataset is transformed to K-space, to obtain the K-space representation of the input image; here, it is possible to provide a mask indicating the K-space positions natively included as or defined by the source data to the DCO. Natively included could mean, e.g., for an input image such K-space positions captured by the input image up to a cut-off spatial frequency defined by Nyquist's theorem. K-space values can be selected from the K-space representation of the input image by the DCO within the mask. For example, for a super-resolution reconstruction without partial Fourier, the mask includes all the K-space positions of the input low-resolution image. If there is partial Fourier, only the acquired measurements defining the source data will be included in the mask.

Using DCOs as outlined above, the reconstruction can have an increased stability and robustness. For example, considering the case of the super-resolution reconstruction, the hard DCO according to Eq. 2 would ensure that the reconstruction algorithm only changes the high spatial frequencies in the reconstructed image vis-á-vis the input image, which high spatial frequency are not available in the source data of the input dataset defining the input image. The reconstruction would not change the low spatial frequencies where most of the energy of the input image and the reconstructed image is located. The low spatial frequencies are fixed, so that it is not possible to add something that was not present in the original input image or remove something that was present in the original input image in this frequency band.

More formally, in the case of an image-to-image reconstruction, the DCO can be summarized with the following pseudo code where y is the input of the DCO (i.e., the pre-DCO reconstructed image; which may be labeled a preliminary reconstructed image) and $\hat{y}$ its output (i.e., the post-DCO final reconstructed image), X is the K-space representation of the input image using zero-padding so that the size of X matches the size of the K-space representation of y (denoted Y), mask being a binary matrix the size of Y with ones where the source data is available from the input dataset and zero when not:

$$Y \leftarrow \mathrm{FFT}(y) \tag{1}$$

$$Y \leftarrow \mathrm{where}(\mathrm{mask}, X, Y) \tag{2}$$

$$\hat{y} \leftarrow \mathrm{IFFT}(Y) \tag{3}$$

FFT means fast Fourier transformation; IFFT means inverse fast Fourier transformation and the operation. Where (condition, m,n) is defined as:

$$\mathrm{out}_i = \begin{cases} m_i & \text{if condition}_i \\ n_i & \text{otherwise} \end{cases}$$

I.e., where (mask,X,Y) returns a tensor of elements selected from either X or Y, depending on the mask value.

In such a scenario, according to Eq. 2, the contribution determined by the DCO replaces, for each one of the multiple K-space positions for which the input dataset includes respective source data (i.e., inside the mask), a further respective K-space value provided by the reconstruction algorithm (i.e., the respective element of the preliminary reconstructed image Y) by the respective K-space value associated with the input dataset (i.e., with the respective element of X). Such operation according to Eq. 2 can be labeled as "hard" DCO, because it is a binary selection between either the K-space value of the source data or the K-space value of the K-space representation of the preliminary reconstructed image.

Such a strict replacement of the respective K-space values in the pre-DCO reconstructed image to obtain the post-DCO reconstructed image according to Eq. 2 is only one option. It would also be possible to determine a "soft" contribution of the respective K-space values associated with the input dataset to the K-space representation of the reconstructed image. Such a "soft" DCO is illustrated below:

$$Y \leftarrow \mathrm{FFT}(y)$$

$$Y \leftarrow Y - \lambda \cdot \mathrm{where}(\mathrm{mask}, Y - X, 0)$$

$$\hat{y} \leftarrow \mathrm{IFFT}(Y) \tag{4}$$

The weighting parameter $\lambda$ defines a weighted combination of the K-space value associated with the input dataset (i.e., X) and a respective further K-space value provided by the reconstruction algorithm (i.e., the preliminary reconstructed image Y), according to Eq. 4.

The weighting parameter is configured to suppress the respective further K-space values if compared to the respective K-space value, as evidenced by the subtraction of Eq. 4.

Note that the hard DCO of Eq. 2 is equivalent to the soft DCO of Eq. 4 when $\lambda=1$.

Next, details with respect to the weighting parameter will be explained.

The weighting parameter $\lambda$ may be predefined. It would also be possible that the weighting parameter is trained using machine-learning techniques. For instance, the weighting parameter may be trained end-to-end together with the reconstruction algorithm. I.e., while varying weights of the reconstruction algorithm, it is possible to also vary the value of the weighting parameter.

It would be possible that the value of the weighting parameter varies as a function of the multiple K-space positions. I.e., it would be possible that depending on the particular K-space position, a different value of the weighting parameter is used. In other examples, the value of the weighting parameter may be fixed, i.e., not vary as a function of the K-space position.

By such techniques, it would be possible to define a transition regime of spatial frequencies where the DCO operates less strict or particularly strict. For instance, the transition regime may be located at the edge of the mask, i.e., at the edge of the regime of multiple K-space positions for which the input dataset includes source data. Thereby, a gradual change between preserving source data and relying on reconstructed data can be achieved, overall leading to an increase in quality of the reconstructed image.

As a general rule, various options are available for implementing the image reconstruction algorithm. Some of the options are summarized in TAB. 1 below.

TABLE 1

Examples of image reconstruction algorithms. In examples III and IV, the DCO can thus be implemented as a sequence of gradient steps with a step-size of one.

| | Brief description | Example details |
|---|---|---|
| I | Classic reconstruction algorithm | A manually parameterized reconstruction algorithm may be used. For instance, such reconstruction algorithm may rely on operations such as interpolation, edge sharpening, contrast enhancement, low-/high-pass filtering, blurring operations, etc. to name just a few options. The DCO can be sequentially applied, after the reconstruction algorithm |
| II | Machine-learned reconstruction algorithm | For instance, it would be possible to use a neural network to implement the reconstruction algorithm. For example, if the reconstruction algorithm is implemented as a multi-layer deep neural network, it would be possible that one or more layers towards the output layer or even the output layer itself implement the DCO. For example, the following implementation would be possible for a multi-layer deep neural network: a layer at the end of the multi-layer deep neural network may be added to implement the DCO; this DCO-layer may transform the input of that layer into K-space and then replace all the values at those K-space positions for which there is a corresponding source data available in the input dataset being input into the input layer of the multi-layer deep neural network. Such source data may be natively defined in K-space. It would also be possible to determine the K-space representation of the input image to determine these values. In either case, a skip connection from the input of the multi-layer deep neural network to the DCI-layer may be implemented. After replacing all the values at those K-space positions at which corresponding source data is available, the DCO layer can transform the result of this operation back to the image domain. During a training phase, weights of each layer of the neural network may be set. During the training phase, it would be possible to rely on ground truth data defining a reference reconstructed image of high quality. For instance, it would be possible to obtain the input image by artificially downsampling or otherwise preprocessing the reference reconstructed image. Noise or artifacts could be synthesized. The machine-learned reconstruction algorithm may be trained end-to-end including the DCO, so during the training process the machine-learned reconstruction algorithm is not required to learn to reconstruct the low spatial frequencies and could then use all of its capacity to only focus in predicting the high spatial frequencies, i.e. a much simpler task for which less training data are needed to obtain a satisfying generalization. This can increase the accuracy. |
| III | Iterative optimization | The iterative optimization can include multiple iterations, e.g., so-called Landweber iterations. Other examples include prima-dual or alternating direction method of multipliers. Thereby, a gradient descent optimization can be implemented. By the iterative optimization, it is possible to maximize or minimize a respective goal function that defines the reconstructed image. The multiple iterations can yield a sequence of (temporary) images. Each iteration can include a regularization operation and the DCO. The DCO can be implemented by an appropriately configured forward-measurement model. For example, the DCO executed in a given iteration is based on difference between the K-space source data and synthesized K-space source data of that respective iteration. The synthesized K-space source data is based on a K-space representation of a prior image of the sequence of images and the forward-measurement model. The forward-measurement model can then suppress contributions to the synthesized K-space source data at K-space positions at which the K-space source data has been sampled using the undersampling trajectory, to thereby implement the DCO. For example, such techniques can be used to implement a reconstruction algorithm to reconstruct an MRI image based on an input dataset including K-space source data that is undersampled in accordance with a respective |

TABLE 1-continued

Examples of image reconstruction algorithms. In examples III and IV, the DCO can thus be implemented as a sequence of gradient steps with a step-size of one.

| Brief description | Example details |
|---|---|
| | undersampling trajectory. Acquisition of MRI data can require significant time. To accelerate the data acquisition, it is known to undersample K-space. Missing data can be reconstructed (MRI reconstruction). Various techniques for implementing MRI reconstruction are known. One prior art technique is referred to as compressed sensing. See, e.g., Lustig, Michael, David Donoho, and John M. Pauly. "Sparse MRI: The application of compressed sensing for rapid MR imaging." *Magnetic Resonance in Medicine: An Official Journal of the International Society for Magnetic Resonance in Medicine* 58.6 (2007): 1182-1195; also see Lustig, Michael, et al. "Compressed sensing MRI." IEEE signal processing magazine 25.2 (2008): 72-82. In further detail, such reconstruction relies on representation of MRI images in a wavelet basis in connection with the regularization operation. As described in id., page 13, section "Image Reconstruction", an optimization problem - typically defined in an $\ell^1$-norm - can be defined. The regularization operation is conventionally based on a non-linear $\ell^1$-norm. A classic formulation of the regularization operation is based on sparsity of the MRI image in a transform domain such as a wavelet domain in combination with pseudo-random sampling that can introduce aliasing artifacts that are incoherent in the respective transform domain. Another example would be a Fourier domain, in particular for acquisitions of a dynamically moving target. Another example would be total variation (TV) used in connection with non-Cartesian K-space trajectories such as radial and spiral trajectories. |
| IV  Unrolled deep neural network (sometimes also referred to as variational neural network) | The unrolled deep neural network can include multiple cascades, corresponding to the iterations of scenario III. Here, each cascade can include a respective regularization operation implemented, e.g., by convolutions and/or activations of a respective layer of the unrolled deep neural network. See Hammernik, Kerstin, et al. "Learning a variational network for reconstruction of accelerated MRI data." Magnetic resonance in medicine 79.6 (2018): 3055-3071, as well as Knoll, Florian, et al. "Deep learning methods for parallel magnetic resonance image reconstruction." arXiv preprint arXiv: 1904.01112 (2019). Such techniques are based on the finding that wavelet compositions - as described in example III- can be expressed as a subset of trainable convolutions of a deep neural network such as a convolutional neural network and that soft-thresholding can be used as an activation function in the deep neural network. for implementing the regularization operation is the U-net, see Ronneberger, Olaf, Philipp Fischer, and Thomas Brox. "U-net: Convolutional networks for biomedical image segmentation." International Conference on Medical image computing and computer-assisted intervention. Springer, Cham, 2015. The U-net employs skip-connections between hidden layers and down-sampling and up-sampling of feature maps. |

The implementation of the DCO using the forward-measurement model (FMM) according to examples III and IV of TAB. 1 is explained below for an undersampled MRI input dataset acquired using multiple RF receiver coils having different sensitivity maps.

As the FMM (excluding the undersampling step M) A=FS, with F being the Fourier transform, and S the coil sensitivity mapping is a Parseval tight frame, i.e. such that A*A=S*F*FS=S*S=I, where A*=S*F* is the adjoint operator of A, and I is the identity matrix. The FMM thus yields synthesized source data that can be compared with the source data y.

$$x \leftarrow x - A^*(MAx - y) = A^*((I-M)Ax + y), \quad (5)$$

where y is the source data of the input dataset (i.e., the MRI raw data) which contains zeros where there is no measurement, x is the input into the DCO (in image space; i.e., an image of the sequence of images associated with the given iteration or cascade), and M is the binary mask which contains 1 where there is a measurement (i.e. where corresponding y coefficient is non zero) and zero otherwise.

As can be seen from Eq. 5, the gradient step with step size 1 generalizes the hard DCO described above.

It includes transforming the current image of the sequence of images x to K-space after applying the sensitivity maps (operation Ax) of the FMM, and then, for the coefficients available in y (for which the mask equal 1) replacing coefficients of x with the one of y and then transforming the result back to the image domain with the operator A*. I.e., the FMM suppresses contributions included in the synthesized source data at those K-space positions at which values are available in y.

Figure 1:
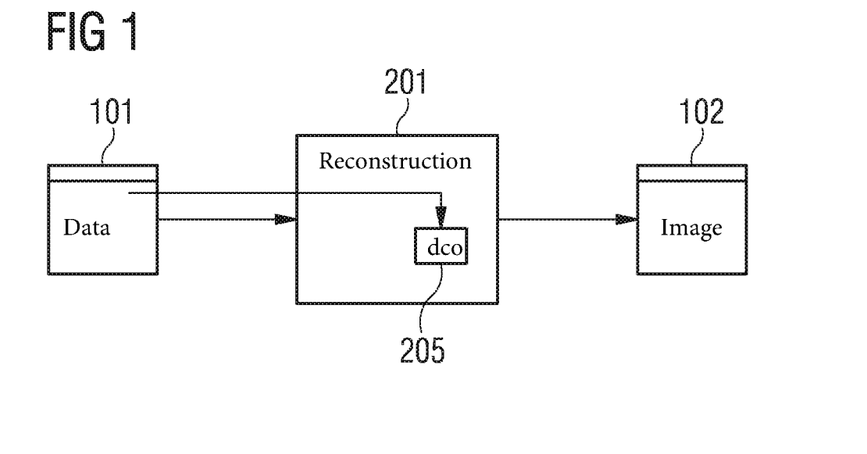
FIG. 1 schematically illustrates a reconstruction algorithm according to various examples.

FIG. 1 schematically illustrates aspects with respect to a reconstruction algorithm 201. The reconstruction algorithm 201 determines a reconstructed image 102 based on an input dataset 101.

According to some examples, the input dataset 101 may directly include an input image; in such a scenario, an image-to-image reconstruction is implemented. Here, the source data corresponds to contrast values for each pixel of the input image. It would also be possible that the input dataset 101 includes raw data that implicitly defines the input image. For instance, the raw source data could be defined in K-space or could be compressed. Pixel values of the input image then have to be inferred from the input dataset, e.g., using the reconstruction algorithm or other preprocessing.

Also illustrated in FIG. 1 is a DCO 205. The illustrated scenario, the DCO 205 is embedded into the reconstruction algorithm 201. As a general rule, it would also be possible that the DCO is executed after completing execution of the reconstruction algorithm 201.

The DCO 205 can alter or change the reconstructed image 102. This makes it possible to define a pre-DCO version of the reconstructed image 102 and a post-DCO version of the reconstructed image 102 (not illustrated in FIG. 1 for sake of simplicity).

As illustrated in FIG. 1, the DCO 205 operates based on the input dataset 101. In particular, the DCO can determine, for multiple K-space positions at which the input dataset includes respective source data (possibly after a Fourier transform of the input image included in the input dataset 101 and to K-space), a contribution of respective K-space values associated with the input dataset to the K-space representation of the reconstructed image 102.

Figure 2:
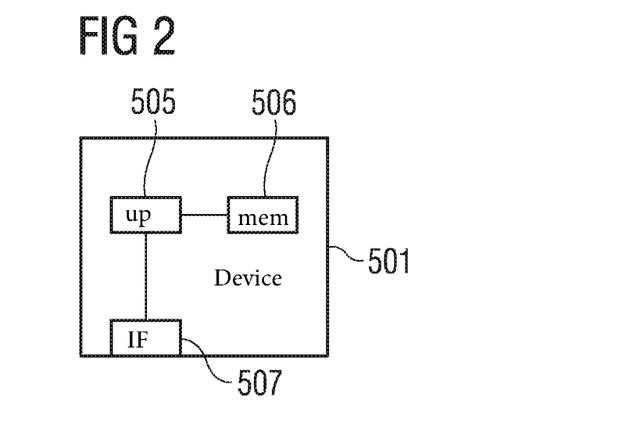
FIG. 2 schematically illustrates a device according to various examples.

FIG. 2 illustrates aspects with respect to a device 501. The device 501 includes a processor 505 and a memory 506. The device 501 also includes an interface 507. For instance, it would be possible that the input dataset 101 is received via the interface 507, e.g., from a database or from a measurement equipment such as a microscope, MRI scanner, a CT scanner, to give just a few examples. The processor 505 can load program code from the memory 506 and execute the program code. Upon loading and executing the program code, the processor 505 can perform one or more of the following: executing a reconstruction algorithm such as the reconstruction algorithm 201; executing a DCO such as the DCO 205; performing a Fourier transform or an inverse Fourier Transform; executing a training process for training machine-learned algorithms; etc.

Figure 3:
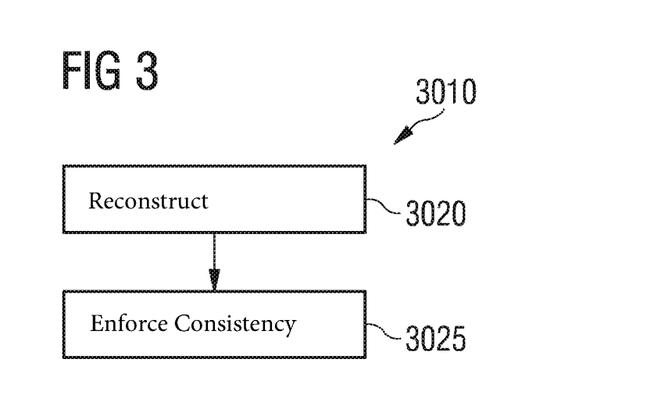
FIG. 3 is a flowchart of a method according to various examples.

FIG. 3 is a flowchart of a method according to various examples. For instance, the method of FIG. 3 could be executed by the processor 505 upon loading program code from the memory 506.

The method of FIG. 3 pertains to inference of a reconstructed image using a reconstruction algorithm such as the reconstruction algorithm 201.

At box 3020, a reconstructed image is determined based on input dataset that defines an input image. For this purpose, the reconstruction algorithm is used. Various types of reconstruction algorithms have been discussed in connection with TAB. 1 and such and other types of reconstruction algorithms can be used in connection with box 3020.

At box 3025, a DCO for enforcing consistency between the input image and the reconstructed image is executed. The DCO can operate on the reconstructed image and change one or more pixel values of the reconstructed image. The DCO can, in particular, operate in K-space. I.e., the method may include a Fourier transform of the reconstructed image into K-space, wherein then K-space values (of the thus defined preliminary version of the reconstructed image before executing the DCO) are adjusted or replaced at one or more K-space positions of the K-space representation of the reconstructed image, followed by an inverse Fourier Transform back into image domain.

The DCO determines, for multiple K-space positions at which the input dataset includes respective source data, a contribution of respective K-space values associated with the input dataset to a K-space representation of the reconstructed image.

While in FIG. 3 the execution of the DCO at box 3025 is shown to be executed after executing the reconstruction algorithm at box 3020, as a general rule, it would be possible that the DCO is executed while still executing the reconstruction algorithm, in particular, in a scenario in which the DCO is embedded in the reconstruction algorithm (a respective scenario will be described later in connection with FIG. 8).

Details with respect to the operation of the DCO are explained next in connection with FIG. 4, FIG. 5, and FIG. 6.

Figure 4:
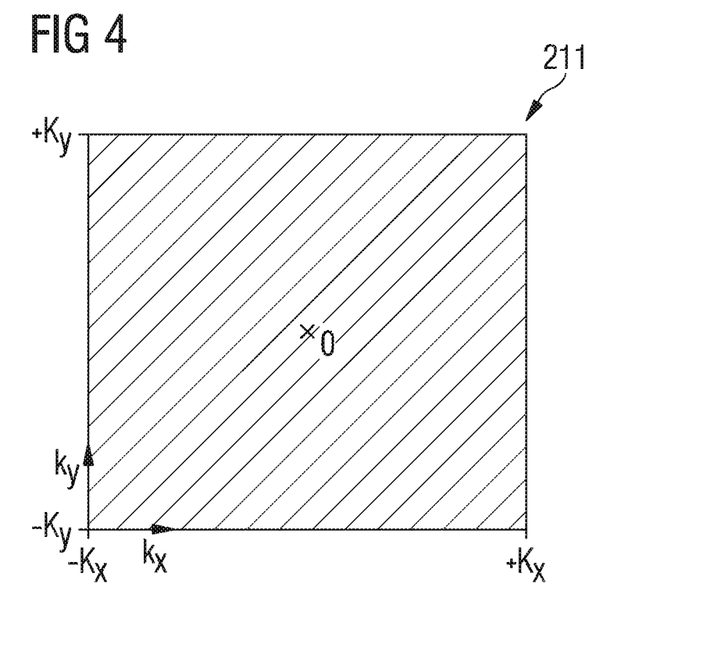
FIG. 4 schematically illustrates a K-space representation of a reconstructed image prior to executing a data-consistency operation according to various examples.

FIG. 4 illustrates the K-space representation of a preliminary reconstructed image 211 prior to applying the DCO (the reconstructed image 211 corresponds to the reconstructed image 102 of FIG. 1, but here is specifically denoting the pre-DCO version).

As illustrated, the K-space representation of the pre-DCO reconstructed image 211 includes K-space values at K-space positions from $-Kx$ to $Kx$ and from $-Ky$ to $+Ky$, respectively (illustrated by the dashed filling).

Figure 5:
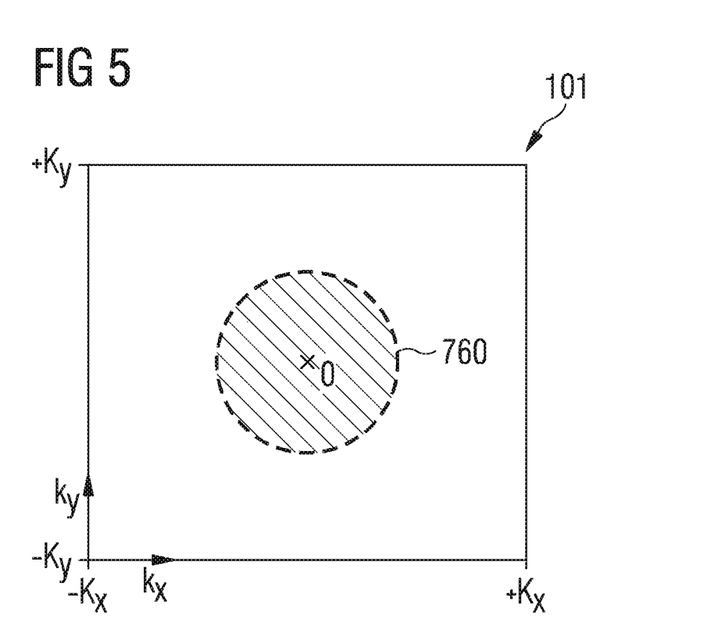
FIG. 5 schematically illustrates an example K-space representation of a K-space representation of an example input image and an example mask segmenting into K-space positions for which the K-space representation includes K-space values and further K-space positions for which the K-space representation does not include K-space values.

FIG. 5 schematically illustrates a K-space representation of the input image defined by the input dataset 101.

The K-space representation may be natively included in the respective source data, e.g., for MRI measurements. It would also be possible to perform a Fourier transform to obtain the K-space representation of the input image defined by the input dataset 101, cf. Eq. 1.

In the illustrated scenario, the K-space representation of the input image defined by the input dataset 101 only includes K-space values at K-space positions close to the K-space center (In FIG. 5, the K-space positions where the respective K-space representation of the reconstructed image 102 and the input image defined by the input dataset 101 include K-space values are also illustrated with a dashed filling).

In FIG. 5, the circumference of a mask 760 that includes all K-space positions for which the K-space representation of the input image includes K-space values is labeled with dashed lines. This mask 760 can define the matrix mask of Eq. 2.

Figure 6:
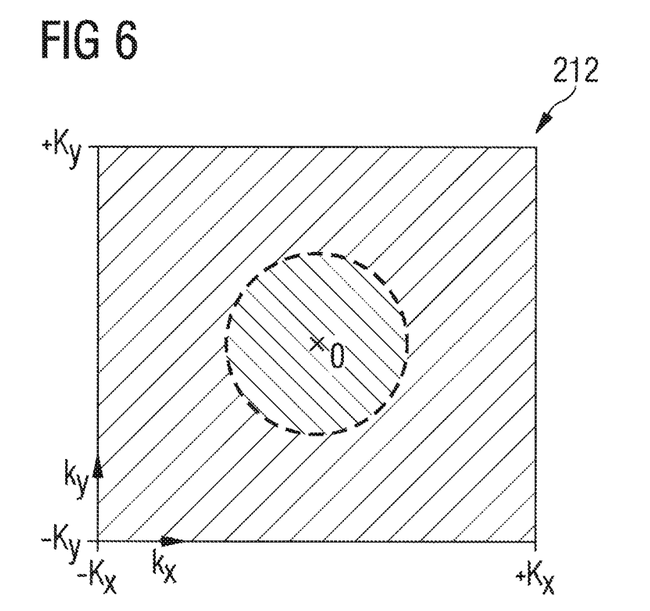
FIG. 6 schematically illustrates a K-space representation of a reconstructed image after executing a data-consistency operation according to various examples.

FIG. 6 schematically illustrates the K-space representation of the reconstructed image 212 after applying the DCO (post-DCO reconstructed image). As illustrated in FIG. 6, the K-space values of the K-space representation of the input image defined by the input dataset 101 have replaced the respective K-space values provided by the reconstruction algorithm, i.e., included in the pre-DCO reconstructed image 211 of FIG. 4. This corresponds to the DCO according to Eq. 2. Other K-space values (for which the input dataset does not include K-space values) in the pre-DCO reconstructed image 211—i.e., away from the center, outside the mask 760—are preserved in the post-DCO reconstructed image 212.

Instead of such a replacement of the respective K-space values of the pre-DCO reconstructed image 211 by the respective K-space values associated with the input dataset, it would also be possible to implement a weighted combination, e.g., using a weighting parameter as discussed above in connection with Eq. 4. The weighting parameter can be configured to suppress the respective K-space values provided by the reconstruction algorithm 201 if compared to the respective K-space values of the input image. This means that while the pre-DCO reconstructed image 211 at and around the K-space center has K-space values determined by the reconstruction algorithm 201, the post-DCO reconstructed image 212 includes, at and around the K-space center, K-space values determined only to a certain degree by the reconstruction algorithm 201, but also based on the K-space representation of the input image. Thus, the influence of the reconstruction algorithm 201 is suppressed. The degree of suppression is controlled by the value or values of the weighting parameter.

Figure 7:
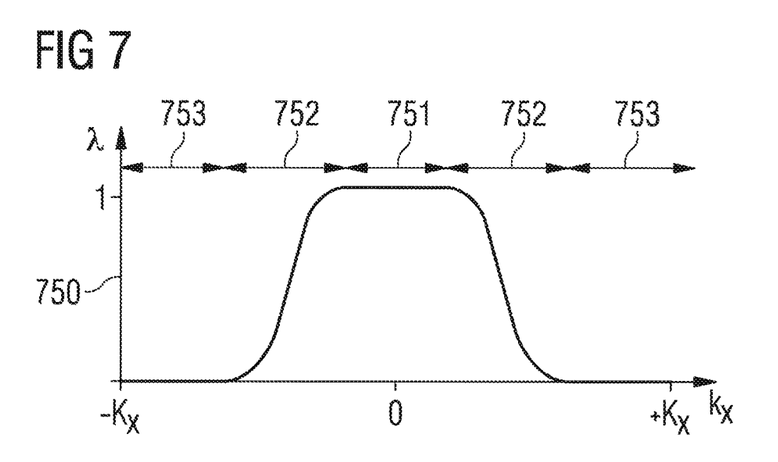
FIG. 7 schematically illustrates a dependency of values of a weighting factor on K-space positions according to various examples.

FIG. 7 illustrates aspects with respect to the weighting parameter 750. As illustrated in FIG. 7, the weighting parameter 750 (cf. Eq. 4, λ)—more accurately, its values—can vary as a function of the K-space position.

The specific configuration of the dependency of the values of the weighting parameter 750 on the K-space position can vary according to different examples. In the illustrated example of FIG. 7, the values of the weighting parameter 750 define three regimes 751-753.

In regime 751—at and around the K-space center—the DCO replaces the K-space values of the pre-DCO reconstructed image 211 by the K-space values of the K-space representation of the input image (λ=1). In regime 752, the DCO implements a weighted combination of the K-space values of the pre-DCO reconstructed image 211 and the K-space values of the K-space representation of the input image. In regime 753, the K-space representation of the input image does not include any K-space values (cf. FIG. 5); and accordingly, the K-space values of the K-space representation of the pre-DCO reconstructed image 211 prevail and are immediately included in the post-DCO reconstructed image 212. By such setting of the dependency of the values of the weighting parameter 750 on the K-space position, it is possible to smoothly transition between preserving the K-space values of the K-space representation of the input image in regime 751 and using the reconstructed K-space values of the K-space representation of the reconstructed image in regime 753. Thereby, an overall improved reconstructed image can be obtained.

For instance, the shape of the spatial dependency of the values of the weighting parameter as illustrated in FIG. 7 could be manually parametrized or predefined. It would also be possible that the value or values of the weighting parameter are determined using a machine-learned process (as will be explained later in connection with FIG. 9 and FIG. 10). In particular, and end-to-end learning of the reconstruction algorithm 2012 together with the value or values of the weighting parameter 750 could be implemented.

Figure 8:
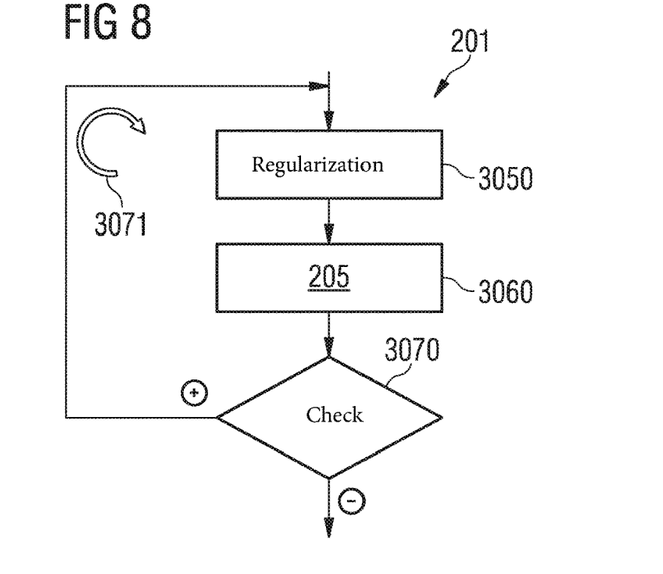
FIG. 8 is a flowchart of a method implementing a reconstruction algorithm including multiple iterations or cascades according to various examples.

FIG. 8 is a flowchart of a method according to various examples. FIG. 8 illustrates an example implementation of the reconstruction algorithm 201. For illustration, the method of FIG. 8 could be executed by the processor 505 of the device 501, upon loading program code from the memory 506.

The reconstruction algorithm 201 according to the method of FIG. 8 implements a multi-step reconstruction, including multiple iterations or cascades 3071. For instance, an iterative optimization or an unrolled deep neural network could be used to implement the reconstruction algorithm 201 according to the method of FIG. 8.

Each iteration or cascade 3071 includes a regularization operation, box 3050; and a DCO at box 3060.

A concrete implementation of box 3050 and box 3060 could be based on Knoll, Florian, et al. "Deep learning methods for parallel magnetic resonance image reconstruction." *arXiv preprint arXiv:*1904.01112 (2019): equation 12. Here, the left term included in the bracket corresponds to the regularization operation of box 3050. The DCO applied at box 3060 can be implemented by the FMM according to Eq. 5. Eq. 5 corresponds to a modified version of the right-hand term in Knoll et al., Eq. 12 in that the FMM is modified to suppress contributions to the synthesized K-space source data at K-space positions at which the K-space source data has been sampled using the undersampling trajectory. Thereby, the FMM implements the DCO.

Note that in Eq. 12 of Knoll et al, the index t counts iterations/cascades and the respective sequence of MRI images is denoted with $u^t$.

Then, at box 3070, it is checked whether a further iteration or cascade 3071 is required; and, in the affirmative, box 3050 and box 3060 are re-executed.

It would be possible that at box 3070 it is checked whether a certain predefined count of iterations or cascades 3071 has been reached. This can be an abort criterion. Other abort criteria are conceivable, e.g., as defined by the optimization method (convergence into a minimum), e.g., gradient descent. It could be checked whether a further layer of the unrolled neural network is available.

Figure 9:
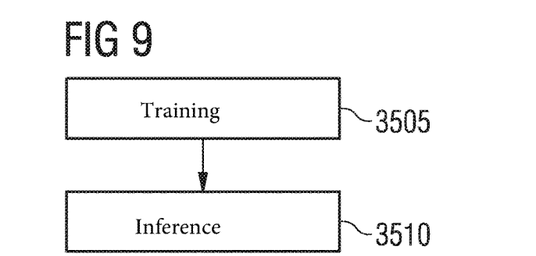
FIG. 9 is a flowchart of a method according to various examples.

FIG. 9 is a flowchart of a method according to various examples. FIG. 9 illustrates a training phase at box 3505 and an inference phase at box 3510.

In a training process of the training phase of box 3505, weights of a machine-learned reconstruction algorithm can be set by implementing a respective training process based on a ground truth. The training process could be executed by the processor or 505 of the device 501 upon loading program code from the memory 506 and executing the program code.

Then, the trained reconstruction algorithm can be used for image reconstruction tasks during inference at box 3510 when no ground truth is available.

Details with respect to the inference have been discussed above. Next, details with respect to the training process of the training phase at box 3505 will be explained below.

Figure 10:
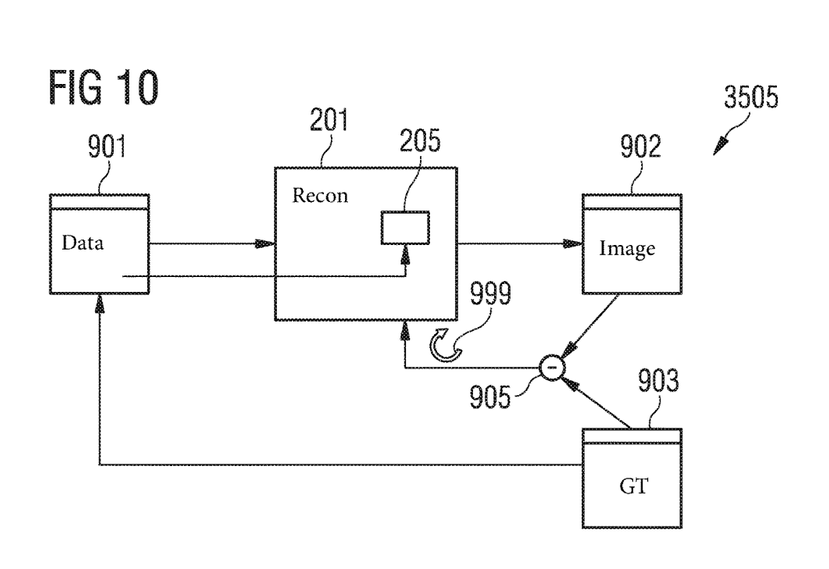
FIG. 10 schematically illustrates a training process for training a machine-learned reconstruction algorithm according to various examples.

FIG. 10 illustrates aspects with respect to training of a machine-learned reconstruction algorithm 201 configured to determine a reconstructed image based on an input dataset (cf. FIG. 1).

As illustrated in FIG. 10, a ground truth image 903 is available. The ground truth image 903 can have desired properties to be achieved by the reconstruction algorithm 201, e.g., a particularly high resolution, suppressed or no artifacts, etc.

The reconstruction algorithm 201 is initially in a untrained state or has only been partly trained. I.e., weights of, e.g., one or more layers have not been accurately set. The purpose of the training process is to accurately set respective parameters of the reconstruction algorithm.

FIG. 10 also illustrates that a training dataset 901 is available. The training dataset 901 is associated with the ground truth image 903. Specifically, the training dataset 901 can define an input image generally corresponding to the ground truth image 903, yet including artifacts or noise or being of lower resolution; i.e., including characteristics that are to be suppressed or mitigated by the reconstruction algorithm 201.

The training dataset 901 can be obtained from measurements or can be inferred from the ground truth image 903 (as illustrated in FIG. 10), e.g., by artificially introducing synthesized artifacts or downsampling the resolution, to give just a few options.

Also illustrated is a reference image 902 determined based on the training dataset 901 by using the reconstruction algorithm 201 (in its respective training state). Further, the reference image 902 is obtained after executing the DCO 205.

It is then possible to determine a loss based on the loss function 905 by comparing the reference image 902 with the ground truth image 903. Deviations are penalized. Based on the loss obtained from the loss function 905, the training state of the reconstruction algorithm 201 is changed, e.g., by changing weights of one or more layers, e.g., using backpropagation.

On the other hand, at least in some examples, the DCO can remain fixed during the training process. The DCO can be predefined, e.g., according to Eq. 2 or Eq. 4 or Eq. 5.

Yet, in some examples it would be possible to also change the value or values of the weighting parameter 750 being part of the DCO 205 during the training process. I.e., the weighting parameter 750 of the DCO 205 and the reconstruction algorithm can be trained end-to-end.

Such training process is iteratively executed in multiple iterations 999. An iterative optimization is thus implementing the training process of the training phase of box 3505.

Summarizing, at least the following EXAMPLES have been disclosed:

EXAMPLE 1. A computer-implemented method, comprising:
- based on an input dataset (101) defining an input image, determining a reconstructed image (102, 211, 212) using a reconstruction algorithm (201), and
- executing a data-consistency operation (205) for enforcing consistency between the input image and the reconstructed image (102, 211, 212), wherein the data-consistency operation (205) determines, for multiple K-space positions at which the input dataset (101) comprises respective source data, a contribution of respective K-space values associated with the input dataset (101) to a K-space representation of the reconstructed image (102, 211, 212).

EXAMPLE 2. The computer-implemented method of EXAMPLE 1, wherein the contribution replaces, for each one of the multiple K-space positions, a further respective K-space value provided by the reconstruction algorithm (201) by the respective K-space value associated with the input dataset (101).

EXAMPLE 3. The computer-implemented method of EXAMPLE 1, wherein the contribution implements, for each one of the multiple K-space positions, a weighted combination of the K-space value associated with the input dataset (101) and a respective further K-space value provided by the reconstruction algorithm (201) in accordance with a weighting parameter (750), the weighting parameter (750) being configured to suppress the respective further K-space value if compared to the respective K-space value.

EXAMPLE 4. The computer-implemented method of EXAMPLE 3, wherein the reconstruction algorithm (201) is machine-learned in a training phase (3510), wherein the weighting parameter (750) is trained end-to-end with the reconstruction algorithm (201).

EXAMPLE 5. The computer-implemented method of EXAMPLE 3 or 4, wherein the weighting parameter (750) varies as a function of the multiple K-space positions.

EXAMPLE 6. The computer-implemented method of any one of EXAMPLES 2 to 5, wherein the reconstruction algorithm (201) is configured to provide a preliminary reconstructed image (102, 211), the further K-space values being determined based on the preliminary reconstructed image (102, 211).

EXAMPLE 7. The computer-implemented method of any one of the preceding EXAMPLES,
wherein the input dataset (101) comprises the input image, wherein the method further comprises:
- transforming the input image into K-space to obtain a K-space representation of the input image, wherein the K-space values are selected from the K-space representation of the input image within a mask (760) limited to such K-space positions natively defined by the source data.

EXAMPLE 8. The computer-implemented method of any one of EXAMPLES 1 to 7, wherein the source data of the input dataset (101) defines the input image in K-space, the source data being undersampled in accordance with an undersampling trajectory,
wherein the reconstruction algorithm (201) comprises an iterative optimization, the iterative optimization comprising multiple iterations (3071),
wherein the data-consistency operation (205) is executed for each iteration of the multiple iterations, to thereby obtain a sequence of images,
wherein the data-consistency operation (205) is executed, in a given iteration of the multiple iterations, to enforce consistency between the source data and synthesized source data, the synthesized source data being based on a K-space representation of a prior image of the sequence of images and a forward-measurement model, the forward-measurement model suppressing contributions to the synthesized source data at K-space positions at which the source data has been sampled using the undersampling trajectory.

EXAMPLE 9. The computer-implemented method of any one of EXAMPLES 1 to 7, wherein the source data of the input dataset (101) defines the input image in K-space, the source data being undersampled in accordance with an undersampling trajectory,
wherein the reconstruction algorithm (201) comprises an unrolled neural network comprising multiple cascades (3071) associated with different layers of the unrolled neural network,
wherein the data-consistency operation (205) is executed for each one of the multiple cascades, to thereby obtain a sequence of images,
wherein the data-consistency operation (205) is executed, in a given cascade, to enforce consistency between the source data and synthesized source data, the synthesized source data being based on a K-space representation of a prior image of the sequence of images and a forward-measurement model, the forward-measurement model suppressing contributions to the synthesized source data at K-space positions at which the source data has been sampled using the undersampling trajectory.

EXAMPLE 10. The computer-implemented method of any one of the preceding EXAMPLES, wherein the reconstruction algorithm (201) comprises multiple iterations or cascades, wherein a regularization operation and a forward-measurement model are executed in each one of the multiple iterations or cascades, the forward-measurement model implementing the data-consistency operation (205).

EXAMPLE 11. The computer-implemented method of any one of the preceding EXAMPLES, wherein the reconstruction algorithm (201) comprises a machine-learned neural network, and wherein the machine-learned neural network is trained end-to-end including the data-consistency operation (205).

EXAMPLE 12. The computer-implemented method of any one of the preceding EXAMPLES, wherein the reconstructed image (102, 211, 212) has an increased resolution if compared to the input image.

EXAMPLE 13. The computer-implemented method of any one of the preceding EXAMPLES, wherein the reconstructed image (102, 211, 212) has reduced aliasing artifacts if compared to the input image.

EXAMPLE 14. The computer-implemented method of any one of the preceding EXAMPLES, wherein, for multiple further K-space positions at which the input image does not comprise the source data, further respective K-space values provided by the reconstruction algorithm (201) are preserved in the reconstructed image (102, 211, 212) by the data-consistency operation (205).

EXAMPLE 15. A computer-implemented method of training a machine-learned reconstruction algorithm (201), the method comprising:
  training the machine-learned reconstruction algorithm (201) using a loss function (905) which is based on a difference between a ground truth image (903) and a reference image (902), the reference image (902) being determined based on a training dataset (901) associated with the ground truth image (903) and using the machine-learned reconstruction algorithm (201), and further based on executing a data-consistency operation (205),
  wherein the data-consistency operation (205) determines, for multiple K-space positions at which the training dataset (901) comprises respective source data, a contribution of respective K-space values associated with the training dataset (901) to a K-space representation of the reference image (902).

EXAMPLE 16. The computer-implemented method of EXAMPLE 15, wherein the contribution implements, for each one of the multiple K-space positions, a weighted combination of the K-space value associated with the training dataset and a respective further K-space value provided by the machine-learned reconstruction algorithm (201) in accordance with a weighting parameter (750), the weighting parameter (750) being configured to suppress the respective further K-space values if compared to the respective K-space value, wherein one or more values of the weighting parameter (750) are adjusted during said training.

EXAMPLE 17. The computer-implemented method of EXAMPLE 15, wherein the data-consistency operation (205) is predefined and not adjusted during said training.

EXAMPLE 18. A device (501) comprising a processor (502) configured to:
  based on an input dataset (101) defining an input image, determine a reconstructed image using a reconstruction algorithm (201),
  execute a data-consistency operation (205) for enforcing consistency between the input image and the reconstructed image,
  wherein the data-consistency operation (205) determines, for multiple K-space positions at which the input dataset (101) comprises respective source data, a contribution of respective K-space values associated with the input dataset (101) to a K-space representation of the reconstructed image.

EXAMPLE 19. The device of EXAMPLE 18, wherein the processor is configured to perform the method of any one of EXAMPLEs 1 to 14.

EXAMPLE 20. A device configured to train a machine-learned reconstruction algorithm (201), the device comprising a processor, the processor being configured to:
  train the machine-learned reconstruction algorithm (201) using a loss function which is based on a difference between a ground truth image and a reference image, the reference image being obtained by executing, to a training dataset, the machine-learned reconstruction algorithm (201) and further executing a data-consistency operation (205),
  wherein the data-consistency operation (205) determines, for multiple K-space positions at which the training dataset comprises respective source data, a contribution of respective K-space values associated with the training dataset to a K-space representation of the reference image.

EXAMPLE 21. The device of EXAMPLE 20, wherein the processor is configured to perform the method of any one of EXAMPLEs 15 to 17.

EXAMPLE 22. A computer program or a computer-program product or a computer-readable storage medium comprising program code, the program code being loadable and executable by a processor, wherein the processor, upon loading and executing the program code performs the method of any one of EXAMPLEs 1 to 17.

Although the invention has been shown and described with respect to certain preferred embodiments, equivalents and modifications will occur to others skilled in the art upon the reading and understanding of the specification. The present invention includes all such equivalents and modifications and is limited only by the scope of the appended claims.

The invention claimed is:

1. A computer-implemented method comprising:
  based on an input dataset defining an input image, determining a reconstructed image using a reconstruction algorithm, and
  executing a data-consistency operation enforcing consistency between the input image and the reconstructed image,
  wherein the data-consistency operation determines, for multiple K-space positions at which the input dataset comprises respective source data, a contribution of respective K-space values associated with the input dataset to a K-space representation of the reconstructed image.

2. The computer-implemented method of claim 1, wherein the contribution replaces, for each one of the multiple K-space positions, a further respective K-space value provided by the reconstruction algorithm by the respective K-space value associated with the input dataset.

3. The computer-implemented method of claim 2, wherein the reconstruction algorithm is configured to provide a preliminary reconstructed image, the further K-space values being determined based on the preliminary reconstructed image.

4. The computer-implemented method of claim 1, wherein the contribution implements, for each one of the multiple K-space positions, a weighted combination of the K-space value associated with the input dataset and a respective further K-space value provided by the reconstruction algorithm in accordance with a weighting parameter, the weighting parameter being configured to suppress the respective further K-space value when compared to the respective K-space value.

5. The computer-implemented method of claim 4, wherein the reconstruction algorithm is machine-learned in a training phase, and wherein the weighting parameter is trained end-to-end with the reconstruction algorithm.

6. The computer-implemented method of claim 5, wherein the weighting parameter varies as a function of the multiple K-space positions.

7. The computer-implemented method of claim 6, wherein the reconstruction algorithm is configured to provide a preliminary reconstructed image, the further K-space values being determined based on the preliminary reconstructed image.

8. The computer-implemented method of claim 4, wherein the weighting parameter varies as a function of the multiple K-space positions.

9. The computer-implemented method of claim 4,
wherein the source data of the input dataset defines the input image in K-space, the source data being undersampled in accordance with an undersampling trajectory,
wherein the reconstruction algorithm comprises an iterative optimization, the iterative optimization comprising multiple iterations,
wherein the data-consistency operation is executed for each iteration of the multiple iterations, to thereby obtain a sequence of images, and
wherein the data-consistency operation is executed, in a given iteration of the multiple iterations, to enforce consistency between the source data and synthesized source data, the synthesized source data being based on a K-space representation of a prior image of the sequence of images and a forward-measurement model, the forward-measurement model suppressing contributions to the synthesized source data at K-space positions at which the source data has been sampled using the undersampling trajectory.

10. The computer-implemented method of claim 4,
wherein the source data of the input dataset defines the input image in K-space, the source data being undersampled in accordance with an undersampling trajectory,
wherein the reconstruction algorithm comprises an unrolled neural network comprising multiple cascades (3071) associated with different layers of the unrolled neural network,
wherein the data-consistency operation is executed for each one of the multiple cascades, to thereby obtain a sequence of images, and
wherein the data-consistency operation is executed, in a given cascade, to enforce consistency between the source data and synthesized source data, the synthesized source data being based on a K-space representation of a prior image of the sequence of images and a forward-measurement model, the forward-measurement model suppressing contributions to the synthesized source data at K-space positions at which the source data has been sampled using the undersampling trajectory.

11. The computer-implemented method of claim 1, wherein the input dataset comprises the input image,
wherein the method further comprises transforming the input image into K-space to obtain a K-space representation of the input image, and
wherein the K-space values are selected from the K-space representation of the input image within a mask limited to such K-space positions natively defined by the source data.

12. The computer-implemented method of claim 1,
wherein the source data of the input dataset defines the input image in K-space, the source data being undersampled in accordance with an undersampling trajectory,
wherein the reconstruction algorithm comprises an iterative optimization, the iterative optimization comprising multiple iterations,
wherein the data-consistency operation is executed for each iteration of the multiple iterations, to thereby obtain a sequence of images, and
wherein the data-consistency operation is executed, in a given iteration of the multiple iterations, to enforce consistency between the source data and synthesized source data, the synthesized source data being based on a K-space representation of a prior image of the sequence of images and a forward-measurement model, the forward-measurement model suppressing contributions to the synthesized source data at K-space positions at which the source data has been sampled using the undersampling trajectory.

13. The computer-implemented method of claim 1,
wherein the source data of the input dataset defines the input image in K-space, the source data being undersampled in accordance with an undersampling trajectory,
wherein the reconstruction algorithm comprises an unrolled neural network comprising multiple cascades associated with different layers of the unrolled neural network,
wherein the data-consistency operation is executed for each one of the multiple cascades, to thereby obtain a sequence of images, and
wherein the data-consistency operation is executed, in a given cascade, to enforce consistency between the source data and synthesized source data, the synthesized source data being based on a K-space representation of a prior image of the sequence of images and a forward-measurement model, the forward-measurement model suppressing contributions to the synthesized source data at K-space positions at which the source data has been sampled using the undersampling trajectory.

14. The computer-implemented method of claim 1, wherein the reconstruction algorithm comprises multiple iterations or cascades, wherein a regularization operation and a forward-measurement model are executed in each one of the multiple iterations or cascades, the forward-measurement model implementing the data-consistency operation.

15. The computer-implemented method of claim 1, wherein the reconstruction algorithm comprises a machine-learned neural network, and wherein the machine-learned neural network is trained end-to-end including the data-consistency operation.

16. The computer-implemented method of claim 1, wherein, for multiple further K-space positions at which the input image does not comprise the source data, further respective K-space values provided by the reconstruction algorithm are preserved in the reconstructed image by the data-consistency operation.

17. A computer-implemented method of training a machine-learned reconstruction, the method comprising:
training the machine-learned reconstruction using a loss function based on a difference between a ground truth image and a reference image, the reference image being determined based on a training dataset associated with the ground truth image and using the machine-learned reconstruction, and further based on executing a data-consistency operation,
wherein the data-consistency operation determines, for multiple K-space positions at which the training dataset comprises respective source data, a contribution of respective K-space values associated with the training dataset to a K-space representation of the reference image.

18. The computer-implemented method of claim 17, wherein the contribution implements, for each one of the multiple K-space positions, a weighted combination of the K-space value associated with the training dataset and a respective further K-space value provided by the machine-learned reconstruction in accordance with a weighting parameter, the weighting parameter being configured to suppress the respective further K-space values when compared to the respective K-space value,
wherein one or more values of the weighting parameter are adjusted during said training.

19. The computer-implemented method of claim 17, wherein the data-consistency operation is predefined and not adjusted during said training.

\* \* \* \* \*